(12) United States Patent
Walker et al.

(10) Patent No.: US 9,808,553 B2
(45) Date of Patent: Nov. 7, 2017

(54) HAEMOSTATIC WOUND DRESSING

(71) Applicant: Haemostatix Limited, Nottingham, Nottinghamshire (GB)

(72) Inventors: Greg Walker, Dunedin (NZ); Sarah Margaret Middleton, Nottingham (GB)

(73) Assignee: HAEMOSTATIX LIMITED, Nottingham, Nottinghamshire (GB)

( * ) Notice: Subject to any disclaimer, the term of this patent is extended or adjusted under 35 U.S.C. 154(b) by 0 days.

(21) Appl. No.: 14/376,023

(22) PCT Filed: Feb. 1, 2013

(86) PCT No.: PCT/GB2013/050237
§ 371 (c)(1),
(2) Date: Jul. 31, 2014

(87) PCT Pub. No.: WO2013/114132
PCT Pub. Date: Aug. 8, 2013

(65) Prior Publication Data
US 2015/0071985 A1    Mar. 12, 2015

(30) Foreign Application Priority Data

Feb. 1, 2012 (GB) .................................. 1201751.3

(51) Int. Cl.
| | | |
|---|---|---|
| A61K 38/00 | (2006.01) | |
| C07K 9/00 | (2006.01) | |
| A61L 24/00 | (2006.01) | |
| A61L 15/32 | (2006.01) | |
| A61L 15/42 | (2006.01) | |
| A61L 15/44 | (2006.01) | |
| A61L 24/10 | (2006.01) | |

(52) U.S. Cl.
CPC ......... *A61L 24/0015* (2013.01); *A61L 15/325* (2013.01); *A61L 15/425* (2013.01); *A61L 15/44* (2013.01); *A61L 24/0036* (2013.01); *A61L 24/0073* (2013.01); *A61L 24/108* (2013.01); *A61L 2300/25* (2013.01); *A61L 2300/252* (2013.01); *A61L 2300/418* (2013.01); *A61L 2300/606* (2013.01); *A61L 2400/04* (2013.01); *A61L 2400/18* (2013.01)

(58) Field of Classification Search
None
See application file for complete search history.

(56) References Cited

U.S. PATENT DOCUMENTS

| | | | |
|---|---|---|---|
| 4,427,651 A | 1/1984 | Stroetmann | |
| 5,902,608 A | 5/1999 | Read et al. | |
| 6,113,948 A | 9/2000 | Heath et al. | |
| 2003/0040692 A1 | 2/2003 | Rothwell et al. | |
| 2003/0212253 A1 | 11/2003 | Hammond et al. | |
| 2004/0101546 A1* | 5/2004 | Gorman | A61K 31/715 424/445 |
| 2005/0037051 A1 | 2/2005 | Pendharkar et al. | |
| 2005/0123588 A1 | 6/2005 | Zhu et al. | |
| 2006/0104970 A1 | 5/2006 | Margel et al. | |
| 2006/0110381 A1 | 5/2006 | Pendharkar et al. | |
| 2006/0204490 A1 | 9/2006 | Pendharkar et al. | |
| 2006/0280713 A1 | 12/2006 | Malessa | |
| 2009/0203619 A1* | 8/2009 | Goodall et al. | 514/14 |
| 2009/0246238 A1 | 10/2009 | Gorman et al. | |
| 2010/0063459 A1* | 3/2010 | Preiss-Bloom et al. | 604/265 |
| 2010/0249044 A1* | 9/2010 | Walker | 514/21.2 |

FOREIGN PATENT DOCUMENTS

| | | |
|---|---|---|
| CN | 101687061 A | 3/2010 |
| RU | 2 326 137 C2 | 6/2007 |
| WO | WO 92/18164 A1 | 10/1992 |
| WO | WO 98/17319 A2 | 4/1998 |
| WO | WO 2005/035002 A1 | 4/2005 |
| WO | 2006/012541 A2 | 2/2006 |
| WO | WO 2007/015107 A2 | 2/2007 |
| WO | WO 2008/065388 A2 | 6/2008 |
| WO | WO 2008065388 A2 * | 6/2008 |

(Continued)

OTHER PUBLICATIONS

Lew W.K. et al., "Clinical Use of Topical Thrombin as a Surgical Hemostat", Biologics: Targest & Therapy 2 (4):593-599 (2008).
Oz M.C. et al., "Controlled Clinical Trial of a Novel Hemostatic Agent in Cardiac Surgery", Ann Thorac Surg 69:1376-1382 (2000).
Medcompare—The Buyer's Guide for Medical Professionals, "Biological Hemostasis Devices Help Make Difficult Procedures Less Irksome"—Technology Spotlight (2 pages).
Invotec International, "Gelita-Spon®"—Absorbable Gelatin, Sponge Products USP (2 pages).

(Continued)

*Primary Examiner* — Jeanette Lieb
(74) *Attorney, Agent, or Firm* — Scully, Scott, Murphy & Presser, P.C.

(57) ABSTRACT

Haemostatic wound dressings are described. The dressings comprise a non-colloidal porous dressing material, and a plurality of fibrinogen-binding peptides immobilised to the non-colloidal porous dressing material, wherein each fibrinogen-binding peptide comprises: an amino acid sequence Gly-Pro-Arg-Xaa (SEQ ID NO: 1) at an amino-terminal end of the peptide, wherein Xaa is any amino acid other than Val, preferably Pro, Sar, or Leu; or an amino acid sequence Gly-His-Arg-Xaa (SEQ ID NO: 2) at an amino-terminal end of the peptide, wherein Xaa is any amino acid other than Pro. The dressings are able to accelerate haemostasis without requiring enzymatic activity. In particular, the dressings to do not rely on the action of exogenous thrombin, and can be stored long-term at room temperature in solution. Methods of making the dressings, and use of the dressings to control bleeding are also described.

25 Claims, 5 Drawing Sheets

(56) References Cited

FOREIGN PATENT DOCUMENTS

| WO | WO 2009/120433 A2 | 10/2009 |
|---|---|---|
| WO | 2010/088469 | 8/2010 |
| WO | WO 2011/006069 A1 | 1/2011 |

OTHER PUBLICATIONS

Medical Hemostat—The Surgical Hemostat Market Comparison and New Hemostat Technology Blog, "Hemostasis Market-Review of Gelfoam, Surgical, Avitene, Floseal, Bovine Thrombin" (Jun. 14, 2009) (16 pages).
FLOSEAL Hemostatic Matrix (5 pages).
Google search results for "Hemostatic Wound Dressing" with accompanying search results: SBIR/STTR "Development of a Hemostatic Wound Dressing Incorporating Lyophilized Platelets" and Wound Dressing Incorporating Lyophilized Platelets-DTIC (3 pages).
International Search Report dated Jun. 27, 2013 received from related Application No. PCT/GB2013/050237.
Written Opinion of the International Searching Authority dated Jun. 27, 2013 received from related Application No. PCT/GB20131050237.

\* cited by examiner a)

Adams et al, J Thromb Thrombolysis 2009 28 (1) 1-5 b)

Fisher's exact test % success over 12 minutes
PeproStat v thrombin 125u/ml P<0.0001
PeproStat v saline P<0.0001
PeproStat v thrombin 1000u/ml NS
% success at 1 minute
PeproStat v thrombin 1000u/ml P=0.0004
% success at 6 minutes
PeproStat v thrombin 1000u/ml P=0.02

Gauze with PeproStat     Gauze with MilliQ water

HAEMOSTATIC WOUND DRESSING

INCORPORATION BY REFERENCE OF SEQUENCE LISTING

The Sequence Listing in an ASCII text file, named as 31239_Sequence_Listing.txt of 2 KB, created on Jul. 30, 2014, and submitted to the United States Patent and Trademark Office via EFS-Web, is incorporated herein by reference.

This invention relates to haemostatic wound dressings, kits and haemostatic agents for formation of haemostatic wound dressings, methods of making the dressings, and use of the dressings to control bleeding, especially severe bleeding such as can occur in surgical practice.

Several topical haemostats for use during surgical procedures are currently available. Absorbable gelatin sponges, such as Gelfoam, are made from porcine gelatin. Gelfoam can absorb over forty times its weight in blood and expand to approximately two hundred percent of its initial volume. The surface of the sponge causes platelet activation via the contact activation pathway of the coagulation cascade. An alternative gelatin-based product, Floseal includes gelatin granules that have been cross-linked so that they do not swell to nearly the same extent as Gelfoam.

Oxidised cellulose sheets, such as Surgicel, are derived from alpha-cellulose, and act at the same point in the contact activation pathway of the coagulation cascade as Gelfoam. When saturated with blood, the sheets swell rapidly into a gelatinous mass. Microfibrillar collagen, such as Avitene, uses collagen derived from bovine skin. It comes in the form of flour or sheets. It binds tightly to blood surfaces and causes minimal swelling. It causes contact activation, but also activates platelets directly.

Topical haemostats are often used in conjunction with thrombin, which generates fibrin from fibrinogen and promotes platelet activation, thereby accelerating blood coagulation. Purified bovine or human thrombin, or recombinant human thrombin, is used. However, bovine thrombin is contaminated with bovine antigen, in particular bovine Factor V. Antibodies generated against this antigen can cross-react with human factor V and lead to life threatening bleeding and, in some circumstances, anaphylaxis and death. Human thrombin has been isolated from pooled plasma of donors in an effort to minimize these risks, but has the potential to transmit blood-borne pathogens, especially viruses. Recently, a recombinant human thrombin has been developed and approved for use by the FDA. It has the advantage of being minimally antigenic and does not carry the risk of viral transmission. However, it is made using a genetically modified Chinese hamster ovary cell line, and so is relatively expensive to produce.

Purified bovine, and recombinant human thrombin preparations are stored at room temperature as a powder which must be reconstituted with saline into solution before use. The FDA-approved purified human thrombin is packaged as a solution, but this can only be stored at room temperature for up to 24 hours; long-term storage requires freezing (Lew and Weaver, Biologics: Targets & Therapy 2008:2(4) 593-599).

A further disadvantage of using thrombin is that it takes time for the enzyme to convert fibrinogen to fibrin, so there is a slight delay before blood coagulation is accelerated.

There is a need, therefore, to provide topical haemostats that can stop severe bleeding quickly and effectively, and that overcome one or more of the above disadvantages of using thrombin.

According to the invention there is provided a haemostatic wound dressing, which comprises a non-colloidal porous dressing material, and a plurality of fibrinogen-binding peptides immobilised to the non-colloidal porous dressing material, wherein each fibrinogen-binding peptide comprises: an amino acid sequence Gly-Pro-Arg-Xaa (SEQ ID NO: 1) at an amino-terminal end of the peptide, wherein Xaa is any amino acid other than Val, preferably Pro, Sar, or Leu; or an amino acid sequence Gly-His-Arg-Xaa (SEQ ID NO: 2) at an amino-terminal end of the peptide, wherein Xaa is any amino acid other than Pro.

Fibrinogen comprises two terminal domains (D-domains), each of which can bind to a fibrinogen-binding peptide. When fibrinogen, for example in plasma or blood, contacts the peptides, a copolymer is formed comprising the fibrinogen-binding peptides and fibrinogen which has characteristics of a fibrin clot. The presence of the fibrinogen-binding peptides in a haemostatic wound dressing of the invention thus accelerates haemostasis.

Haemostatic wound dressings of the invention have surprisingly been found to have significantly better haemostatic properties than a conventional gelatin pad soaked in thrombin.

Haemostatic wound dressings of the invention do not rely on the action of exogenous thrombin. The fibrinogen-binding peptides can be made synthetically and so are minimally antigenic, do not carry the risk of viral transmission, can be made more cheaply than recombinant proteins expressed in mammalian cell lines, and can be stored long-term at room temperature in solution.

Haemostatic wound dressings of the invention do not require enzymatic activity to accelerate haemostasis, and so accelerate haemostasis immediately on contact with fibrinogen.

The term "non-colloidal porous dressing material" is used herein to refer to any non-colloidal porous material that can be topically applied to cover, dress, or protect a wound. Examples of such material include sheets, pads, sponges, foams, films, gauzes, mesh, granules, and beads. Non-colloidal porous dressing material includes material that is suitable for topical application to a wound, but not suitable for injection into the body. In particular, the granules or beads are too large to pass through the lung capillary bed. At least a majority of the granules or beads have a maximum dimension that is greater than 6 µm. The non-colloidal porous dressing material may comprise any suitable chemical. Examples include gelatin, cotton, rayon, polyester, collagen, alginate, and oxidised cellulose. Gelatin is preferred.

Thrombin cleaves peptides (releasing fibrinopeptides A and B) from the amino terminals of the α and β chains of fibrinogen to expose the sequences $NH_2$-GPRV- (SEQ ID NO: 3) and $NH_2$-GHRP- (SEQ ID NO: 4), respectively. The fibrinogen-binding peptides of the haemostatic wound dressing of the invention, therefore, differ in sequence from the sequences exposed by the action of thrombin on fibrinogen. Preferably at least some (more preferably, all) of the fibrinogen-binding peptides comprise the sequence $NH_2$-GPRP- (SEQ ID NO: 5) at the amino terminal end.

Preferably the fibrinogen-binding peptides are each 4-60, preferably 4-30, more preferably 4-10, amino acid residues in length.

The amino-terminal end of each fibrinogen-binding peptide is able to bind to "holes" in the fibrinogen molecule (Weisel, Fibrinogen and Fibrin, Advances in Protein Chemistry, 2005, Vol. 70, pp. 247-299). Thus, any sequence of the fibrinogen-binding peptides that is carboxy-terminal to the four amino acid residues at the amino-terminal end of each peptide is not critical as long as this sequence does not inhibit binding of the amino-terminal end of the peptide to fibrinogen.

In some preferred embodiments of the invention, each fibrinogen-binding peptide is at least 5 amino acid residues long to ensure that the peptide is sufficiently long to engage with high affinity to its binding site in fibrinogen. Thus, it is particularly preferred that each fibrinogen binding peptide is 5-60, 5-30, or 5-10 amino acid residues in length. It is preferred that the fifth amino acid residue from the amino-terminal end of each such fibrinogen-binding peptides is a glycine residue. In other embodiments, each fibrinogen-binding peptide may be at least 6, 7, 8, 9, 10, or 11 amino acid residues in length. It is preferred that each fibrinogen binding peptide is no longer than 60 amino acid residues in length, more preferably no longer than 30 amino acid residues in length.

Preferably each fibrinogen-binding peptide is a synthetic peptide.

Preferably the fibrinogen binding peptides bind to fibrinogen with a dissociation constant of between $10^{-9}$ to $10^{-6}$ M, for example around 10, 20, 30, 40, 50, 60, 70, 80, 90, 100, 110, 120, 130, 140, 150, 200, 250, 300, 350, 400, or more nM. A dissociation constant of around 100 nM is preferred.

The fibrinogen-binding peptides may each have the same sequence, preferably each comprising sequence of SEQ ID NO: 1 at the amino-terminal end. Alternatively, the fibrinogen-binding peptides may comprise peptides of different sequence, as long as each peptide comprises sequence of SEQ ID NO: 1 or SEQ ID NO: 2 at its amino-terminal end.

The plurality of fibrinogen-binding peptides may be covalently or non-covalently immobilised to the non-colloidal porous dressing material.

According to a preferred embodiment of the invention, a plurality of carriers are non-covalently immobilised to the non-colloidal porous dressing material, and a plurality of fibrinogen-binding peptides are immobilised, preferably covalently immobilised, to each carrier.

When fibrinogen, for example in plasma or blood, contacts the fibrinogen-binding peptides immobilised to the carriers it binds to the peptides. Because each fibrinogen molecule can bind two peptides, the fibrinogen molecules become non-covalently cross-linked via the carriers, and a copolymer is formed comprising the carriers and fibrinogen which has characteristics of a fibrin clot.

The carriers may be soluble or insoluble carriers, but are not platelets. The carriers should be suitable for topical administration to a bleeding wound site. The carriers may comprise a soluble or insoluble polymer, for example a protein, a polysaccharide, or a synthetic biocompatible polymer, such as polyethylene glycol, or a combination of any of these. Albumin is a preferred protein carrier.

An insoluble carrier may be a microparticle (including a solid, hollow, or porous microparticle, preferably a substantially spherical microparticle). The microparticle may be formed of any suitable substance, for example cross-linked protein. A suitable protein is albumin (serum-derived or recombinant, human or non-human in sequence). Microparticles suitable for use as insoluble carriers in the present invention may be formed by spray drying human serum albumin (HSA) using well known spray-drying technology, for example as in WO 92/18164. Alternatives to use of microparticles as carriers include liposomes, synthetic polymer particles (such as polylactic acid, polyglycolic acid and poly(lactic/glycolic) acid), or cell membrane fragments.

At least a majority of the carriers preferably have a maximum dimension that is less than 6 μm.

In theory there is no upper limit to the number of fibrinogen-binding peptides per carrier molecule. The optimum number is likely to depend on many factors, such as the nature of the carrier, and the number of reactive groups on each carrier for attaching the fibrinogen-binding peptides. However, it is preferred that on average there are up to 100 fibrinogen-binding peptides per carrier molecule. Preferably, on average there are at least three, preferably at least five fibrinogen-binding peptides per carrier molecule. A preferred range is 10-20 fibrinogen-binding peptides per carrier molecule.

Preferably the fibrinogen-binding peptides are covalently immobilised to the carriers.

The carriers may comprise reactive groups which permit attachment of the fibrinogen-binding peptides. For example, the carriers may comprise thiol moieties or amine moieties on their surface. If the carriers are proteinaceous, the thiol or amine moieties may be provided by side chains of amino acids, for example cysteine or lysine. Alternatively, reactive groups may be added to the carrier. This is particularly advantageous if the carrier is formed from protein, such as HSA. For example, the carrier may be thiolated using a reagent such as 2-iminothiolane (2-IT) which is able to react with primary amine groups on the carrier. Alternatively cystamine may be coupled to carboxyl groups on the carrier in the presence of 1-Ethyl-3-(3-dimethylaminopropyl) carbodiimide hydrochloride (EDC) and N-hydroxysuccinimide (NHS), followed by reductive cleavage of the introduced disulphide bond.

In preferred embodiments, the fibrinogen-binding peptides are covalently immobilised to the carrier via a spacer. A preferred spacer is a non-peptide spacer, for example comprising a hydrophilic polymer such as polyethylene glycol (PEG). In a preferred embodiment, a plurality of peptide conjugates, each comprising a fibrinogen-binding peptide linked to a thiol-reactive group (for example, a maleimide group) by a PEG spacer are reacted with a thiolated carrier (for example prepared using 2-IT or cystamine as described above).

The carriers may be non-covalently immobilised to the non-colloidal porous dressing material by contacting an aqueous solution or suspension of the carriers with the dressing material for sufficiently long that the carriers become immobilised to the dressing material. In a preferred method, the carriers are soaked onto the dressing material.

In other embodiments, each fibrinogen-binding peptide is covalently immobilised directly to the non-colloidal porous dressing material, optionally via a spacer. A preferred spacer is a non-peptide spacer, preferably comprising a hydrophilic polymer such as PEG.

In such embodiments, the non-colloidal porous dressing material preferably comprises granules or beads. In a particularly preferred embodiment, the granules or beads comprise a polymeric substance, for example a protein such as gelatin.

The non-colloidal dressing material may comprise reactive groups which permit attachment of the fibrinogen-binding peptides. For example, the dressing material may comprise thiol moieties or amine moieties on its surface. If the dressing material is proteinaceous, the thiol or amine moieties may be provided by side chains of amino acids, for example cysteine or lysine. Alternatively, reactive groups may be added to the dressing material. This is particularly advantageous if the dressing material is formed from protein, such as gelatin. For example, the dressing material may be thiolated using a reagent such as 2-iminothiolane (2-IT) which is able to react with primary amine groups on the dressing material. Alternatively cystamine may be coupled to carboxyl groups on the dressing material in the presence of 1-Ethyl-3-(3-dimethylaminopropyl) carbodiimide hydrochloride (EDC) and N-hydroxysuccinimide (NHS), followed by reductive cleavage of the introduced disulphide bond.

In preferred embodiments, the fibrinogen-binding peptides are covalently immobilised to the non-colloidal dressing material via a spacer. A preferred spacer is a non-peptide spacer, for example comprising a hydrophilic polymer such as polyethylene glycol (PEG).

In a preferred embodiment, a plurality of peptide conjugates, each comprising a fibrinogen-binding peptide linked to a thiol-reactive group (for example, a maleimide group) by a PEG spacer are reacted with a thiolated dressing material (for example prepared using 2-IT or cystamine as described above).

A haemostatic wound dressing of the invention may be in dry form, preferably in freeze-dried form. Example 5 below shows that a haemostatic wound dressing of the invention retains ability to co-polymerise fibrinogen following rehydration after freeze-drying.

Preferably the wound dressing is sterile. A haemostatic wound dressing of the invention may be provided as a sterile wound dressing ready for administration to a wound.

There is further provided according to the invention a haemostatic wound dressing of the invention packaged with instructions for application of the wound dressing to a wound.

There is also provided according to the invention a kit for formation of a haemostatic wound dressing, which comprises a non-colloidal porous dressing material, and, separately, a haemostatic agent comprising a plurality of carriers and a plurality of fibrinogen-binding peptides immobilised to each carrier, wherein each fibrinogen-binding peptide comprises: an amino acid sequence Gly-Pro-Arg-Xaa (SEQ ID NO: 1) at an amino terminal end of the peptide, wherein Xaa is any amino acid other than Val, preferably Pro, Sar, or Leu; or an amino acid sequence Gly-His-Arg-Xaa (SEQ ID NO: 2) at an amino-terminal end of the peptide, wherein Xaa is any amino acid other than Pro.

The kit may further comprise instructions to apply the agent to the non-colloidal porous dressing material before application of the dressing material to a wound and/or instructions for application of the haemostatic wound dressing to a wound.

There is also provided according to the invention a haemostatic agent comprising a plurality of carriers and a plurality of fibrinogen-binding peptides immobilised to each carrier, wherein each fibrinogen-binding peptide comprises: an amino acid sequence Gly-Pro-Arg-Xaa (SEQ ID NO: 1) at an amino-terminal end of the peptide, wherein Xaa is any amino acid other than Val, preferably Pro, Sar, or Leu; or an amino acid sequence Gly-His-Arg-Xaa (SEQ ID NO: 2) at an amino-terminal end of the peptide, wherein Xaa is any amino acid other than Pro, and wherein the agent is packaged with instructions to apply the agent to a non-colloidal porous dressing material before application of the dressing material to a wound.

Advantageously, the haemostatic agent may be in solution, in suspension, or in dry form, for example freeze-dried form. Example 3 below demonstrates that a haemostatic agent of the invention retains ability to co-polymerise fibrinogen following extraction into solution from a freeze-dried haemostatic wound dressing of the invention. Example 6 shows that a haemostatic agent of the invention is stable in solution for at least six months at 37° C. Thus, if desired, a haemostatic agent of the invention can be stored in solution thereby avoiding the need for reconstitution into solution prior to use.

The invention further provides a method of controlling bleeding, especially severe bleeding, which comprises administering a haemostatic wound dressing of the invention to a wound.

The term "severe bleeding" is used herein to include bleeding that requires intervention (surgical or endoscopic) or decompression of a closed space to stop or control the event, bleeding causing hemodynamic compromise (requiring blood, fluid replacement, inotropic support, or surgical intervention), or bleeding which cannot be controlled by conventional intervention such as manual pressure, cauterization or sutures.

According to the invention there is also provided a method of making a haemostatic wound dressing, which comprises immobilising a plurality of fibrinogen-binding peptides to a non-colloidal porous dressing material, wherein each fibrinogen-binding peptide comprises: an amino acid sequence Gly-Pro-Arg-Xaa (SEQ ID NO: 1) at an amino-terminal end of the peptide, wherein Xaa is any amino acid other than Val, preferably Pro, Sar, or Leu; or an amino acid sequence Gly-His-Arg-Xaa (SEQ ID NO: 2) at an amino-terminal end of the peptide, wherein Xaa is any amino acid other than Pro.

The plurality of fibrinogen-binding peptides may be covalently or non-covalently immobilised to the non-colloidal porous dressing material.

Preferably the plurality of fibrinogen-binding peptides are immobilised to the non-colloidal porous dressing material by immobilising a plurality of carriers to the non-colloidal porous dressing material, wherein a plurality of fibrinogen-binding peptides are immobilised to each carrier.

Such methods may further comprise immobilising a plurality of fibrinogen-binding peptides to each carrier.

Preferably a plurality of carriers are non-covalently immobilised to the non-colloidal porous dressing material, and a plurality of fibrinogen-binding peptides are immobilised, preferably covalently, to each carrier.

Suitable methods for covalently immobilising the fibrinogen-binding peptides to the carriers, optionally via a spacer (preferably a non-peptide spacer, for example comprising a hydrophilic polymer such as PEG), are described above.

Suitable methods for non-covalently immobilising the carriers to the non-colloidal porous dressing material are described above.

Suitable methods for covalently immobilising each fibrinogen-binding peptide directly to the non-colloidal porous dressing material, optionally via a spacer (preferably a non-peptide spacer, for example comprising a hydrophilic polymer such as PEG), are described above.

There is also provided according to the invention a method of making a haemostatic wound dressing, which comprises applying a haemostatic agent to a non-colloidal porous dressing material, wherein the haemostatic agent comprises a plurality of carriers and a plurality of fibrinogen-binding peptides immobilised to each carrier, wherein each fibrinogen-binding peptide comprises: an amino acid sequence Gly-Pro-Arg-Xaa (SEQ ID NO: 1) at an amino terminal end of the peptide, wherein Xaa is any amino acid other than Val, preferably Pro, Sar, or Leu; or an amino acid sequence Gly-His-Arg-Xaa (SEQ ID NO: 2) at an amino-terminal end of the peptide, wherein Xaa is any amino acid other than Pro.

The haemostatic agent may be non-covalently applied to the non-colloidal porous dressing material, for example by contacting an aqueous solution or suspension of the haemostatic agent with the dressing material for sufficiently long that the haemostatic agent becomes immobilised to the dressing material. In a preferred method, the haemostatic agent is soaked onto the dressing material.

Particularly preferred haemostatic wound dressings of the invention comprise a plurality of soluble carriers (preferably soluble protein carriers, such as albumin carriers) to which a plurality of fibrinogen-binding peptides (each peptide preferably comprising an amino acid sequence Gly-Pro-Arg-Pro-Gly- (SEQ ID NO: 6) at the amino-terminal end of the peptide) are covalently immobilised via a non-peptide spacer (suitably a hydrophilic polymer, such as polyehtylene glycol) to each carrier. The carriers are non-covalently immobilised to a non-colloidal porous dressing material (preferably comprising gelatin, such as a gelatin pad, or comprising rayon or polyester). Examples of such haemostatic wound dressings are described in Examples 2, 3, and 4 below.

Further particularly preferred haemostatic wound dressings of the invention comprise a plurality of fibrinogen-binding peptides (each peptide preferably comprising an amino acid sequence Gly-Pro-Arg-Pro-Gly- at the amino-terminal end of the peptide) covalently immobilised via a non-peptide spacer (suitably a hydrophilic polymer, such as polyethylene glycol) directly to a non-colloidal porous dressing material (preferably comprising gelatin, such as gelatin granules). Examples of such haemostatic wound dressings are described in Example 5 below.

Embodiments of the invention are now described by way of example only, with reference to the accompanying drawings in which.

Figure 1:
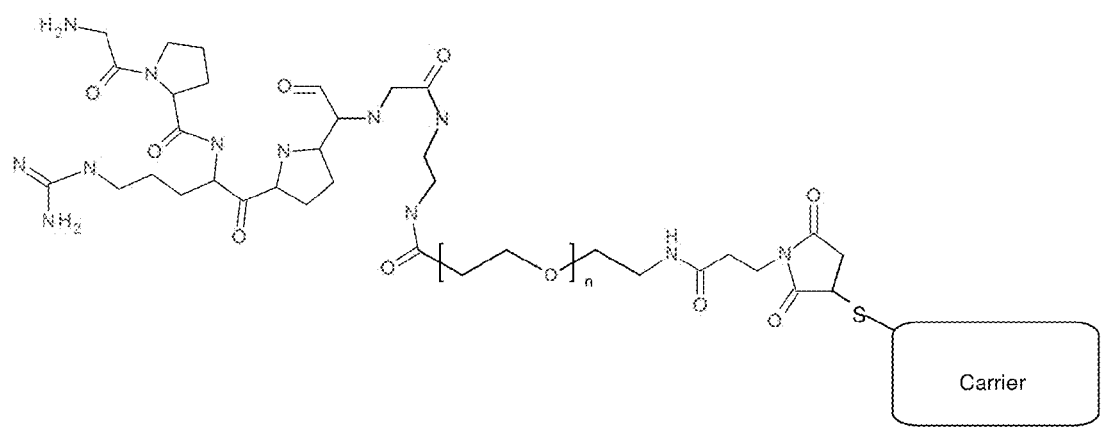
FIG. 1 shows the structure of a preferred example of a fibrinogen-binding peptide covalently immobilised to a carrier (according to preferred embodiments of the invention a plurality of such fibrinogen-binding peptides are covalently immobilised to the carrier—only a single fibrinogen-binding peptide immobilised to the carrier is shown in the figure)
Figure 2:
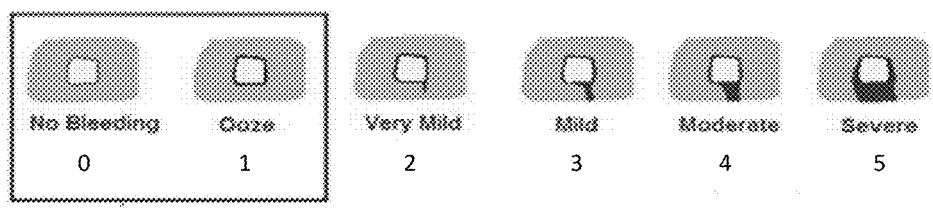
FIG. 2a shows a scheme for assignment of bleeding scores according to Adams et al, *J Thromb Thrombolysis*, 2009, 28(1):1-5.
FIG. 2b is a graph showing the results of an assessment of the haemostatic activity of a haemostatic wound dressing according to a preferred embodiment of the invention.
Figure 2:
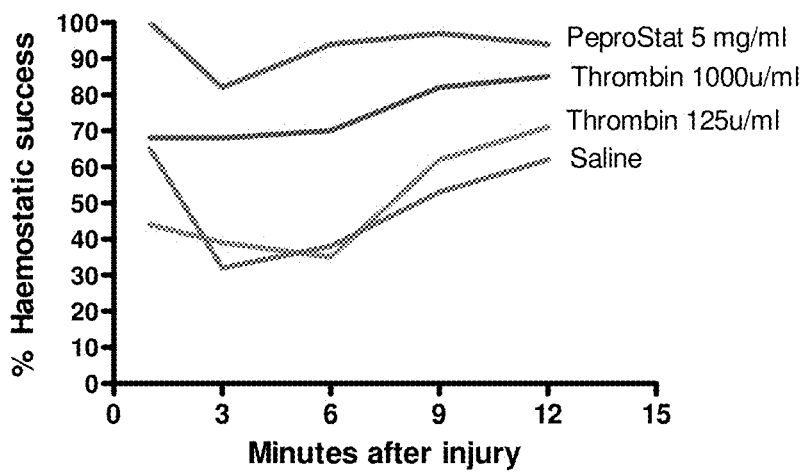

Reference to "clot formation" and "clotting activity" in relation to haemostatic wound dressings and haemostatic agents of the invention is reference to formation of a copolymer comprising the fibrinogen-binding peptides of the dressings or agents and fibrinogen, which has characteristics of a fibrin clot.

EXAMPLE 1

Conjugation of a Fibrinogen-binding Peptide to an Albumin Carrier

This example describes conjugation of a fibrinogen-binding peptide of sequence GPRPG, linked to a maleimide group (Mal) by a polyethylene glycol (PEG) linker, to an albumin carrier. The resulting product is referred to as "PeproStat".

Human serum albumin is diluted to 50 mg/mL in reaction buffer (50 mM sodium phosphate, 150 mM sodium chloride, 100 mM Ethylenediaminetetraacetic acid [EDTA], pH 8.0±0.2) and thiolated by the addition of a sixty-fold molar excess of 2-iminothiolane hydrochloride. After incubation for one hour at room temperature, thiolated albumin is separated from unreacted 2-iminothiolane hydrochloride by tangential flow diafiltration using 20 mM sodium phosphate, 150 mM sodium chloride, 1 mM EDTA pH 7.2±0.2 (filtration buffer).

Peptide conjugation is performed by dissolving peptide (GPRPG-PEG12-maleimide) at a concentration of 50 mg/mL in filtration buffer and adding to thiolated albumin at a ratio of 0.95 mg peptide per 1 mg albumin. Following incubation for one hour at room temperature, excess peptide is removed by dialysing against a 60-fold excess of Tris-buffered saline (TBS; 20 mM Tris, 150 mM sodium chloride pH 7.2±0.2) using dialysis membrane with a molecular weight cut-off of 10-14 KD for at least 16 hours at 4° C., with one change of buffer. Recovered PeproStat is diluted to 5 mg/mL in TBS, sterile filtered through a 0.2 μm filter, dispensed and stored at 4° C.

The protein content of the final product is estimated by measuring absorbance at 280 nm where E(280, 1%)=5.3.

The activity of the final product is investigated using a Sigma Amelung KC4 coagulometer. Briefly, 30 μL test sample at 0.5 mg/ml is added to 100 μL purified human fibrinogen at 3 mg/ml, the KC4 registers clot formation in less than 6 seconds.

The molecular weight of the final product is estimated by SDS-PAGE of reduced samples using 4-15% Tris-glycine precast gels stained with Coomassie by comparison with the band profile of unstained protein ladder.

Product Profile

| Test | Parameter | Profile |
|---|---|---|
| Adsorption at E280 | Total protein | 5 mg/ml |
| Clotting activity | Activity | 0.5 mg/ml clots in <6 seconds |
| SDS PAGE | Molecular weight | 85-120 KD |

EXAMPLE 2

Study of Haemostatic Activity of PeproStat Pre-soaked onto a Gelatin Pad

The haemostatic activity of PeproStat was to be determined using a heparinised rabbit model. However, before using this model, it was important to determine that the product is active in a rabbit, and in particular that the fibrinogen-binding sequence of PeproStat (GPRP-) binds to rabbit fibrinogen. This was done by conjugating a GPRPG peptide to albumin microparticles, which were then incubated with FITC-labelled rabbit fibrinogen. Fluorescent fibrinogen binding to the particles can then be measured using a Flow Cytometer. By this method it was shown that binding of PeproStat to rabbit fibrinogen was comparable to that of human fibrinogen. This confirms published data showing that the relevant rabbit and human fibrinogen binding sequence exposed when thrombin cleaves Fibrinopeptide A from fibrinogen is the same.

The fibrinogen binding sequence (GPRP) in PeproStat is derived from the sequence GPR that is exposed when Fibrinopeptide A is cleaved from fibrinogen by the action of thrombin. The fourth amino acid in the sequence (proline) confers a higher affinity for fibrinogen than the natural cleaved sequence in human fibrinogen which has a valine residue at that position (Laudano and Doolittle Biochemistry 1980, 19: 1013-1019). Laudano and Doolittle have shown that whilst all species share the terminal GPR sequence, there is variation in the amino acid at position four, which is known to affect affinity for fibrinogen. Sequence data shows that rabbit fibrinogen also has a valine residue at position four and therefore rabbit and human fibrinogen might be expected to have comparable affinity for GPRP, as we have found.

A rabbit liver abrasion injury model was used to assess the comparative haemostatic effect of PeproStat, thrombin, or saline soaked onto a gelatin pad. Haemostatic activity was determined in rabbits dosed with heparin at 1000 IU/kg.

A gelatin pad was cut to 2.0×3.0 cm using a scalpel blade. For each treatment, a pad sample was immersed in a 1.5 ml aliquot of test solution (a PeproStat, thrombin, or saline solution). It was then withdrawn and squeezed between gloved fingers to expel air bubbles, then returned to the solution until required.

A superficial circular lesion (diameter 10.3 mm, depth 2-3 mm) was created by abrading the surface of the liver lobe using a Dremel hand drill (Model 395 Type 5, USA; 10,000-35,000 rpm) with a flat surface abrasion stone (Dremel, part no. 85602 USA). Blood exiting the wound was collected for 15 s with a pre-weighed dry swab. The weight of blood collected was used as a measure of bleeding severity. After removal of the swab the pre-soaked test pad was applied, and wet gauze was used to apply gentle pressure to the treated wound for 30 seconds.

Seven injuries can be performed sequentially on each liver, and test pads randomised across the seven sites. 34 tests were performed on each test pad.

Figure 3:
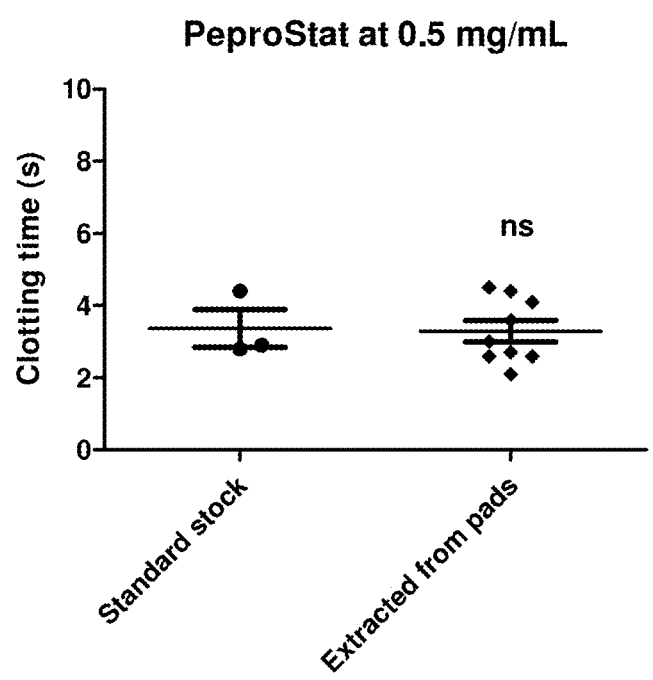
FIG. 3 shows the results of a comparison of the clotting activity of carriers with immobilised fibrinogen-binding peptides recovered from freeze-dried and non freeze-dried haemostatic wound dressings of the invention.

Upon removal of the moist gauze, with the test pad still in place, the wound was evaluated for haemostasis at 1, 3, 6, 9, and 12 minutes, where one minute refers to the time from when the test pad is applied to the wound. Bleeding scores of 0, 1, 2, 3, 4, and 5 are assigned by the surgeon in accordance with the scheme shown in FIG. 3a.

Results

A score of 0 (i.e. no bleeding) is judged as successful haemostasis at each time point. The percentage of 34 treatments (n=34 rabbits) regarded as successful was calculated for each time point. The results are shown in the FIG. 3b.

The results show that PeproStat at a concentration of 5 mg/ml soaked onto the gelatin pad is a significantly better haemostatic agent than saline or thrombin (at 125 units/ml) soaked onto the gelatin pad.

EXAMPLE 3

Freeze Drying of PeproStat onto a Gelatin Pad

To determine the absorbent capacity of the pad, a 40 cm$^2$ gelatin pad was soaked in 10 ml of deionised water. After maximising absorbance by massaging and re-soaking the pad to eliminate all the air, 2 ml of water remained. Therefore it was calculated that the capacity of a 40 cm$^2$ pad was 8 ml.

PeproStat at 10 mg/ml was desalted using an Amicon Ultra centrifugal filter device and diluted to 2.5 mg/ml. A 40 cm$^2$ gelatin pad was soaked in 8 ml PeproStat at 2.5 mg/ml and the pad then squeezed through gloved fingers to remove air bubbles. The pads were left in the solution and gently rocked for 1 hour at room temperature to ensure all the solution was adsorbed.

The pad was then freeze-dried using a bench-top Freeze Dryer.

The shelves of the Freeze-Dryer were equilibrated at −36° C., and the pads placed on the pre-frozen shelf and subjected to thermal treatment steps bringing the temperature up to −20° C. over a period of 270 minutes.

Primary drying was accomplished over 800 minutes decreasing the vacuum from 800 mTorr with a concomitant increase in temperature to 20° C.

The freeze-dried pad was stored in a desiccator.

The success of the freeze-drying was analysed by comparison of the clotting activity of PeproStat recovered from the pad after freeze-drying with PeproStat which had not been freeze-dried.

The 40 cm$^2$ pad containing 40 mg PeproStat was found to weigh 440 mg in total after freeze-drying.

25 mg was cut from the pad and placed in a weighing boat. The dry PeproStat was extracted from the pad by thoroughly soaking the pad in 1 mL 10 mM sodium phosphate, 150 mM sodium chloride buffer, pH 7.2±0.2, and then squeezing the resultant solution out of the pad. The extraction procedure was performed on four separate occasions. The protein content of recovered PeproStat in the solution was measured using a 5 μm C8 Symmetry Reverse Phase HPLC from a calibration curve constructed from dilutions of standard PeproStat.

Analysis of the extracted protein showed that 90-95% of the protein was recovered from the pad.

The clotting activity of the sample was measured using a Sigma Amelung KC-4 coagulometer which measures the time taken to form a clot. The analysis of clotting activity of the eluted PeproStat was compared with that of non freeze-dried PeproStat.

Results

Figure 4:
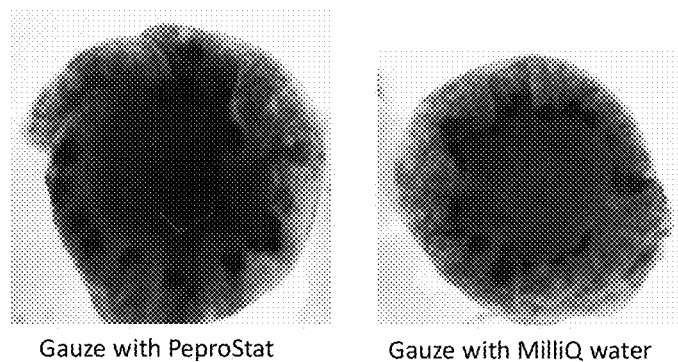
FIG. 4 shows the results of an assessment of the haemostatic activity of a haemostatic wound dressing according to a further preferred embodiment of the invention.
Figure 4:
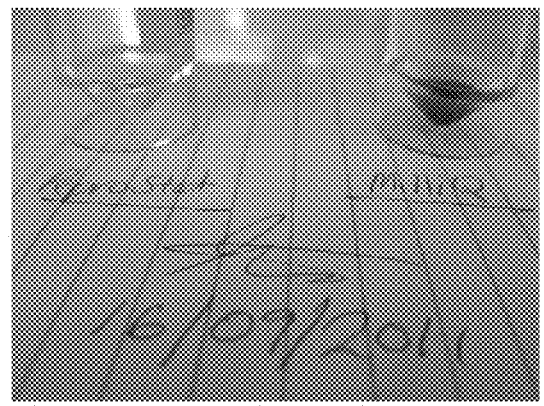

The results are shown in FIG. 4.

There was no significant difference between the clotting activity of control non freeze-dried PeproStat and PeproStat from the freeze-dried pad when tested in the KC-4 coagulometer at 0.5 mg/mL.

EXAMPLE 4

Haemostatic Activity of PeproStat Soaked onto Rayon/Polyester Porous Dressing

The haemostatic activity of 0.5 mL PeproStat at 5 mg/mL soaked onto a polyester/rayon blend was measured using a blood impedance method as follows:

A double layer of the polyester/rayon gauze was stretched over a Universal container with an internal diameter of 2.5 cm and the area of gauze covering the open tube was marked. The gauze was removed from the tube and 0.5 mL PeproStat at 5 mg/mL was applied to the marked circle; 0.5 ml water was applied to a second dressing marked in the same manner as a control.

The Universal containers were weighed and the soaked gauzes stretched across the mouth of the tube. 4×0.5 mL citrated whole blood was then applied sequentially to the soaked gauze, and blood transfer through the gauze was measured by the weight of blood in the tube.

Results

Figure 5:
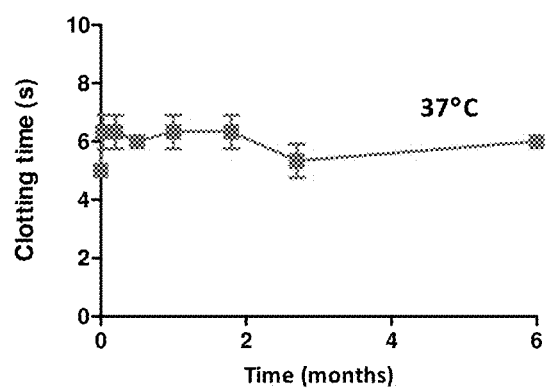
FIG. 5 shows the results of stability testing of fibrinogen-binding peptides immobilised to HSA carrier in solution stored at 37° C. for up to 6 months.

The mean weight of blood passing through the gauze plus PeproStat was 0.009 g±0.016 g (n=3) compared with 0.695 g±0.721 g passing through the control gauze (n=3) as illustrated in a representative picture shown in FIG. 5.

EXAMPLE 5

Haemostatic Properties of Gelatin Carriers with Immobilised Fibrinogen-binding Peptides This example describes preparation of two different preferred haemostatic wound dressings of the invention, and their haemostatic properties. Both dressings comprise a plurality of gelatin carriers, with a plurality of fibrinogen-binding peptides covalently immobilised to each carrier via a PEG linker. In this example, the gelatin carriers (or granules) provide the non-colloidal porous dressing material.

To prepare the first dressing, 2-iminothiolane was used to covalently attach a plurality of fibrinogen-binding peptide-PEG linker conjugates to the gelatin carrier. To prepare the second dressing, cystamine moieties were conjugated to the carboxyl groups of gelatin in the presence of 1-Ethyl-3-(3-dimethylaminopropyl) carbodiimide hydrochloride (EDC) and N-hydroxysuccinimide (NHS), followed by reductive cleavage of the introduced disulphide bond to generate a free thiol for attachment of the fibrinogen-binding peptide.

Preparation of Gelatin Granules Conjugated with GPRPG-PEG-12-Mal Using 2-Iminothiolane Gelatin granules were thiolated using 2-iminothiolane which modifies amine residues. The method used was that of Kommareddy S, Amiji M, 2005, *Bioconjugate Chem* 16: 1423-1432.

1 g of gelatin granules were weighed and hydrated in 40 ml of a buffer containing 50 mM sodium phosphate, 0.15M NaCl, 0.1M EDTA pH 8.0±0.2, by mixing on a roller mixer for 10 minutes at room temperature. 102 g of 2-iminothiolane are added to the hydrated gelatin and mixed on a roller mixer for 1 hour. The granules were then spun at 500 rpm-RCF 28 for 2 minutes, the supernatant removed, and volume replaced with 20 mM sodium phosphate, 0.15M NaCl, 0.1 M EDTA pH 7.2±0.2. This was repeated four times to remove the 2-iminothiolane.

An Ellman's assay was performed to measure the number of —SH groups introduced onto the gelatin. Ellman's reagent 5,5'dithiobis(2-nitrobenzoic acid) reacts with sulphydryls under slightly alkaline conditions to release the highly chromogenic compound, 5-thio-2 nitrobenzoic acid (TNB) Ellman G L. (1959) Arch Bichem.Biophys. 82 70-77.

Following quantitation of the —SH groups, 2.5 ml GPRPG-PEG-12-Mal at 50 mg/ml was added to the granules and roller mixed for 1 hour. The granules were then washed four times with distilled water to remove excess peptide. A slurry of the granules was placed in a plastic container and dried by incubating at 37° C. for 15 hours.

Preparation of Gelatin Granules Conjugated with GPRPG-PEG-12-Mal Using EDC/Cystamine Chemistry 2.2 g of gelatin granules were weighed out and hydrated in 80 mL of 50 mM MES buffer, pH 6.0, for 15 minutes on a roller mixer. 625 mg of Cystamine, 350 mg of 1-Ethyl-3-(3-dimethylaminopropyl) carbodiimide hydrochloride (EDC), and 130 mg of N-hydroxysuccinimide (NHS) were weighed out and added to hydrated granules. The reaction mixture was left for 2 hours on a roller mixer at ambient temperature, and then split into two 50 mL tubes. The granules were then washed and spun at 500 rpm with 4×40 mL volumes of MES buffer. 200 μL of 1M tris(2-carboxyethyl)phosphine (TCEP) stock was added to each tube and left for 10 minutes on the roller mixer at ambient temperature. A repeat washing with 4 volumes of MES was followed by an Ellman's Assay to determine free —SH.

7.2 mL of GPRPG-PEG-12-Mal at 50 mg/ml was mixed with 10.45 mL of N-ethyl-maleimide and then 8.8 mL of the mixture was added to each tube. The reaction was left for 1 hour on a roller mixer at ambient temperature.

Reactions were washed and spun at 800 rpm with 4 volumes of Milli-Q water to remove excess peptide and N-ethyl-maleimide. Granules were then poured into a plastic box, covered with Nescofilm, the Nescofilm pierced and placed in a bench-top Freeze-Dryer for drying as follows:

Drying Process for Conjugated Granules

The shelves of the freeze-dryer were equilibrated at −36° C., and the gelatin granules placed on the pre-frozen shelf and subjected to thermal treatment steps bringing the temperature up to −20° C. over a period of 270 minutes. Primary drying was accomplished over 800 minutes decreasing the vacuum from 800 mTorr with a concomitant increase in temperature to 20° C. The freeze-dried granules were stored in a desiccator prior to testing.

Testing of Dry Gelatin Granules in a Plug Disintegration Test 100 mg of dry conjugated gelatin granules were packed into a 3 ml syringe, and then 0.5 ml tris-buffered saline (TBS) (0.02M Tris, 0.15M NaCl, pH 7.2±0.2) was added, using a syringe connector, to suspend the granules. 0.5 ml thrombin at 500 u/ml or 0.5 ml TBS was added to 100 mg "blank" (non-conjugated gelatin granules). Using a syringe connector, TBS was passed from another 3 ml syringe into each formulation to suspend it. Each suspension was then mixed by passing it between the syringes approximately 40 times.

The gelatin slurry was added to a third 3 ml syringe and the syringe plunger used to form a plug. 0.2 ml of plasma was then injected into the plug, and left to stand for 3 minutes. The bottom of the syringe was cut off and the plug pushed out into a 50 ml tube containing 0.9% saline. The tube was then mixed on a vortex mixer for up to 10 minutes. The plug was then scored over a period of 10 minutes as follows:

0=plug disintegrated entirely; 2=small lumps present (2-5 mm in size); 5=larger lumps present (5-8 mm); 8=large plug intact, signs of erosion; 10=plug completely intact.

Results

| Sample | Time point (minutes) | Score |
| --- | --- | --- |
| Conjugated granules | 1 | 10 |
|  | 3 | 10 |
|  | 7 | 10 |
|  | 10 | 10 |
| Thrombin/granules | 1 | 10 |
|  | 3 | 10 |
|  | 7 | 10 |
|  | 10 | 10 |
| TBS/granules | 1 | 0 |
|  | 3 | 0 |
|  | 7 | 0 |
|  | 10 | 0 |

The results show that the mechanical durability of the plug formed using the conjugated gelatin granules of the invention is equivalent to that of the non-conjugated granules mixed with thrombin.

EXAMPLE 6

Stability of Fibrinogen-binding Peptides Immobilised to Carrier in Solution

This example describes the results of stability testing of fibrinogen-binding peptides immobilised to carriers in solution at 37° C.

PeproStat (comprising fibrinogen-binding peptides, each of sequence GPRPG immobilised to HSA carrier) was stored in solution for 6 months at 37° C. At time zero, and various times during the storage period, samples of the stored solution were assayed for ability to form a co-polymer with fibrinogen, as follows:

Fibrinogen was diluted in 10 mM HEPES, 0.15M NaCl, pH 7.3+/1 0.2 to 6 mg/ml. 25 μl PeproStat at 5 mg/ml was added to 400 μl of the diluted fibrinogen, and the time taken for formation of a visual clot comprising a co-polymer of PeproStat and fibrinogen was recorded.

The results are shown in FIG. 5, and demonstrate that PeproStat is stable in solution at 37° C. for at least 6 months.

The invention claimed is:

1. A haemostatic wound dressing, which comprises a non-colloidal porous dressing material, and a plurality of fibrinogen-binding peptides immobilized to the non-colloidal porous dressing material, wherein each fibrinogen-binding peptide comprises:
   an amino acid sequence Gly-Pro-Arg-Xaa (SEQ ID NO: 1) at an amino-terminal end of the peptide, wherein Xaa is any amino acid other than Val; or
   an amino acid sequence Gly-His-Arg-Xaa (SEQ ID NO: 2) at an amino-terminal end of the peptide, wherein Xaa is any amino acid other than Pro,
   wherein the non-colloidal porous dressing material comprises a sheet, pad, sponge, foam, film, gauze, mesh, granules or beads, wherein if the non-collodial porous dressing material comprises granules or beads, a majority of the granules or beads have a maximum dimension that is greater than 6 µm, and
   wherein a plurality of carriers are immobilized to the non-colloidal porous dressing material, and the plurality fibrinogen binding peptides are covalently immobilized to each carrier.

2. A wound dressing according to claim 1, wherein each fibrinogen-binding peptide is covalently immobilised to the carrier by a non-peptide spacer.

3. A wound dressing according to claim 2, wherein the non-peptide spacer comprises a hydrophilic polymer.

4. A wound dressing according to claim 3, wherein the hydrophilic polymer comprises polyethylene glycol.

5. A wound dressing according to claim 1, wherein the carriers are soluble carriers.

6. A wound dressing according to claim 1, wherein the non-colloidal porous dressing material comprises a sheet, pad, sponge, foam, film, gauze or mesh.

7. A wound dressing according to claim 1, wherein the non-colloidal porous dressing material comprises granules, and wherein a majority of the granules have a maximum dimension that is greater than 6 µm.

8. A wound dressing according to claim 1, wherein the non-colloidal porous dressing material comprises gelatin, cotton, rayon, polyester, collagen, alginate, or oxidised cellulose.

9. A wound dressing according to claim 1 which is in dry form.

10. A wound dressing according to claim 1 which is in freeze-dried form.

11. A wound dressing according to claim 1, wherein the fibrinogen-binding peptides are each 4-60 amino acid residues long.

12. A kit for formation of a haemostatic wound dressing, which comprises a non-colloidal porous dressing material, and, separately, a haemostatic agent comprising a plurality of carriers and a plurality of fibrinogen-binding peptides immobilized to each carrier, wherein each fibrinogen-binding peptide comprises: an amino acid sequence Gly-Pro-Arg-Xaa (SEQ ID NO: 1) at an amino terminal end of the peptide, wherein Xaa is any amino acid other than Val; or an amino acid sequence Gly-His-Arg-Xaa (SEQ ID NO: 2) at an amino-terminal end of the peptide, wherein Xaa is any amino acid other than Pro; wherein the non-colloidal porous dressing material comprises a sheet, pad, sponge, foam, film, gauze, mesh, granules or beads, wherein if the non-colloidal porous dressing material comprises granules or beads, a majority of the granules or beads have a maximum dimension that is greater than 6 µm; and wherein the plurality of carriers are immobilized to the non-colloidal porous dressing material, and the plurality fibrinogen binding peptides are covalently immobilized to each carrier.

13. A method of controlling bleeding, which comprises administering a haemostatic wound dressing according to claim 1 to a wound.

14. A wound dressing according to claim 1, wherein Xaa is Pro, Sar, or Leu.

15. A kit according to claim 12, wherein Xaa is Pro, Sar, or Leu.

16. A wound dressing according to claim 1, wherein said non-colloidal porous dressing comprises granules or beads, and wherein at least a majority of said granules or beads have a maximum dimension that is greater than 6 µm.

17. A kit according to claim 12, wherein said non-colloidal porous dressing comprises granules or beads, and wherein at least a majority of said granules or beads have a maximum dimension that is greater than 6 µm.

18. A haemostatic wound dressing, which comprises a non-colloidal porous dressing material, and a plurality of fibrinogen-binding peptides immobilized to the non-colloidal porous dressing material, wherein each fibrinogen-binding peptide comprises:
   an amino acid sequence Gly-Pro-Arg-Xaa (SEQ ID NO: 1) at an amino-terminal end of the peptide, wherein Xaa is any amino acid other than Val; or
   an amino acid sequence Gly-His-Arg-Xaa (SEQ ID NO: 2) at an amino-terminal end of the peptide, wherein Xaa is any amino acid other than Pro, wherein the non-colloidal porous dressing material comprises granules or beads, wherein a majority of the granules or beads have a maximum dimension that is greater than 6 µm, and wherein the plurality of fibrinogen binding peptides are covalently immobilized to the non-colloidal porous dressing material.

19. A wound dressing according to claim 18, wherein the non-colloidal porous dressing material comprises gelatin granules, and wherein a majority of the gelatin granules have a maximum dimension that is greater than 6 µm.

20. A wound dressing according to claim 18, wherein each fibrinogen-binding peptide is covalently immobilised to the non-colloidal porous dressing material by a non-peptide spacer.

21. A wound dressing according to claim 20, wherein the non-peptide spacer comprises a hydrophilic polymer.

22. A wound dressing according to claim 21, wherein the hydrophilic polymer comprises polyethylene glycol.

23. A wound dressing according to claim 18 which is in dry form.

24. A wound dressing according to claim 23 which is in freeze-dried form.

25. A kit for formation of a haemostatic wound dressing, which comprises a non-colloidal porous dressing material, and, separately, a haemostatic agent comprising a plurality of fibrinogen-binding peptides, wherein each fibrinogen-binding peptide comprises: an amino acid sequence Gly-Pro-Arg-Xaa (SEQ ID NO: 1) at an amino terminal end of the peptide, wherein Xaa is any amino acid other than Val; or an amino acid sequence Gly-His-Arg-Xaa (SEQ ID NO: 2) at an amino-terminal end of the peptide, wherein Xaa is any amino acid other than Pro; wherein the non-colloidal porous dressing material comprises granules or beads, wherein a majority of the granules or beads have a maximum dimension that is greater than 6 µm; and wherein the fibrinogen-binding peptides are covalently immobilized to the non-colloidal porous dressing material.

* * * * *

SEQUENCE LISTING

```
<160> NUMBER OF SEQ ID NOS: 6

<210> SEQ ID NO 1
<211> LENGTH: 4
<212> TYPE: PRT
<213> ORGANISM: Artificial Sequence
<220> FEATURE:
<223> OTHER INFORMATION: Synthetic fibrinogen-binding peptide
<220> FEATURE:
<221> NAME/KEY: MISC_FEATURE
<222> LOCATION: (4)..(4)
<223> OTHER INFORMATION: Xaa can be any naturally occurring amino acid,
      excluding Val

<400> SEQUENCE: 1

Gly Pro Arg Xaa
1

<210> SEQ ID NO 2
<211> LENGTH: 4
<212> TYPE: PRT
<213> ORGANISM: Artificial Sequence
<220> FEATURE:
<223> OTHER INFORMATION: Synthetic fibrinogen-binding peptide
<220> FEATURE:
<221> NAME/KEY: MISC_FEATURE
<222> LOCATION: (4)..(4)
<223> OTHER INFORMATION: Xaa can be any naturally occurring amino acid,
      excluding Pro

<400> SEQUENCE: 2

Gly His Arg Xaa
1

<210> SEQ ID NO 3
<211> LENGTH: 4
<212> TYPE: PRT
<213> ORGANISM: Homo sapiens

<400> SEQUENCE: 3

Gly Pro Arg Val
1

<210> SEQ ID NO 4
<211> LENGTH: 4
<212> TYPE: PRT
<213> ORGANISM: Homo sapiens

<400> SEQUENCE: 4

Gly His Arg Pro
1

<210> SEQ ID NO 5
<211> LENGTH: 4
<212> TYPE: PRT
<213> ORGANISM: Artificial Sequence
<220> FEATURE:
```

```
-continued

<223> OTHER INFORMATION: Synthetic fibrinogen-binding peptide

<400> SEQUENCE: 5

Gly Pro Arg Pro
1

<210> SEQ ID NO 6
<211> LENGTH: 5
<212> TYPE: PRT
<213> ORGANISM: Artificial Sequence
<220> FEATURE:
<223> OTHER INFORMATION: Synthetic fibrinogen-binding peptide

<400> SEQUENCE: 6

Gly Pro Arg Pro Gly
1               5
```